United States Patent [19]

Czajkowski et al.

[11] 4,231,786
[45] Nov. 4, 1980

[54] COMPOSITIONS AND METHODS FOR REDUCING HERBICIDAL INJURY

[75] Inventors: Albert J. Czajkowski, Maryland Heights; David E. Schafer, St. Louis, both of Mo.

[73] Assignee: Monsanto Company, St. Louis, Mo.

[21] Appl. No.: 536,527

[22] Filed: Dec. 26, 1974

[51] Int. Cl.³ ............................................ A01N 37/20
[52] U.S. Cl. ...................................... 71/100; 71/101; 71/111
[58] Field of Search .......................... 71/100, 101, 111

[56] References Cited
U.S. PATENT DOCUMENTS 3,330,643 7/1967 Harman et al. ..................... 71/100

OTHER PUBLICATIONS

"Pesticides '72", Chemical Week, Jun. 21, 1972, p. 42.

Primary Examiner—Catherine L. Mills
Attorney, Agent, or Firm—Richard H. Shear; Donald W. Peterson

[57] ABSTRACT

A method and compositions for reducing injury to crops, especially wheat and sorghum, by thiolcarbamate herbicides employing compounds having in common the base structure wherein Y and Y' are oxygen or sulfur.

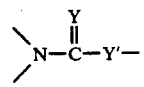

5 Claims, No Drawings

COMPOSITIONS AND METHODS FOR REDUCING HERBICIDAL INJURY

This invention relates to novel compositions and methods for reducing or nullifying injury to young crop plants by selective herbicides. More specifically, this invention relates to novel compositions and methods for reducing injury to young crop plants by herbicides, such as thiolcarbamate herbicides, which comprises treating the habitat of the crop plant or the seed of the crop plant prior to planting, with an antagonistic agent for the herbicide.

Thiolcarbamate herbicides such as triallate, diallate, S-ethyl-N,N-dipropylthiolcarbamate (also referred to as EPTC), S-ethyl-N-ethylthiolcyclohexanecarbamate (cycloate), S-propyl-N-butyl-N-ethylthiolcarbamate (pebulate), S-ethyl-N,N-diisobutylthiolcarbamate (butylate), S-propyl-N,N-dipropylthiolcarbamate (vernolate), and the like are very useful for controlling certain weeds in the presence of other growing plants. However, many of these herbicides injure certain crop plants, slowing growth and development at application rates necessary to stunt or kill the weeds. As a consequence, certain of these herbicides can not be employed for controlling weeds in the presence of certain crops, some of which crops are important commodities in the world food supply. Obviously, there is a need for a method of reducing or nullifying the injury of the crop plant by the thiolcarbamate herbicide while not affecting the herbicidal action on the weed to be controlled.

There is provided by this invention a novel method of reducing or nullifying injury to the desired crop plant by thiolcarbamate herbicides which does not interfere with the herbicidal action on the weed to be controlled. There are also provided novel compositions for treating the soil or the crop seed to reduce or nullify injury to the crop by thiolcarbamate herbicides.

The compounds which are useful in reducing or eliminating crop injury are sometimes referred to as antagonistic agents, antidote compounds, or safening agents. Antagonistic agents for the purpose of this invention are defined as compounds which counteract the herbicidal action of thiolcarbamate herbicides, thereby reducing or nullifying injury to the crop plant, the crop or crop seed by the herbicide but which exhibit little or no toxicity to the crop plant, the crop or crop seed at safening effective rates of application. Although the mechanism by which these compounds reduce the herbicidal activity of the thiolcarbamate herbicide on crop plants without reducing the effective control of undesired plants or weeds, is not fully understood, the herbicide test program has confirmed the phenomenon for a wide variety of compounds having in common the base structure

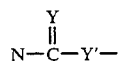

wherein Y and Y' are oxygen or sulfur. These compounds when employed with a thiolcarbamate herbicide reduce the injury to crop plants by the thiolcarbamate herbicide, particularly the injury to wheat and sorghum. The compounds which are preferred antagonistic agents with thiolcarbamate herbicides for the selective control of undesired plants in the presence of wheat and sorghum are described by the formula

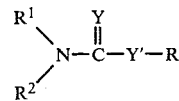

wherein Y and Y' are each independently oxygen or sulfur and, when Y and Y' are both sulfur, R is alkyl, alkenyl, alkynyl, haloalkenyl, substituted alkyl or phenyl, $R^1$ is hydrogen, alkyl, haloalkenyl or alkenyl and $R^2$ is alkyl, phenyl substituted alkyl, phenyl or substituted phenyl, or $R^1$ and $R^2$ when taken together are alkylene of the empirical formula $—C_nH_{2n}—$ wherein n is an integer of from 4 through 8, inclusive, having from 4 through 8 carbons in a continuous chain between the nitrogen terminal bonds or a group of the formula

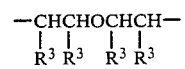

wherein each $R^3$ is independently hydrogen, halo or lower alkyl; when one of Y and Y' is oxygen, R is alkyl, substituted alkyl, phenyl, substituted phenyl, alkenyl or haloalkenyl, $R^1$ is hydrogen, alkyl or substituted alkyl and $R^2$ is alkyl, phenyl or substituted phenyl, lower alkoxybenzyl or $R^1$ and $R^2$ when taken together are alkylene of the empirical formula $—C_nH_{2n}$ wherein n is an integer of from 4 through 8, inclusive, having from 4 through 8 carbons in a continuous chain between the nitrogen terminal bonds or a group of the formula

wherein each $R^3$ is indentently hydrogen, halo or lower alkyl; and when both Y and Y' are oxygen, R is alkyl or phenyl, $R^1$ is alkyl, phenyl or substituted phenyl and $R^2$ is hydrogen, alkyl, alkenyl or haloalkenyl or R and $R^1$ when taken together are alkylene of the empirical formula $—C_nH_{2n}$ wherein n is an integer of from 4 through 8, inclusive, having from 4 through 8 carbons in a continuous chain between the nitrogen terminal bonds or a group of the formula

wherein each $R^3$ is independently hydrogen, halo or lower alkyl.

The amount of such antagonistic agents employed in methods and compositions of this invention will very according to the particular thiolcarbamate herbicide with which the agent is employed and the rate of application of the herbicide. In each instance the amount of antagonistic agent employed is a safening effective amount. By a safening effective amount is meant an amount which reduces crop injury by the thiolcarbamate herbicide. In the tests employed in illustrating this invention, the amount of crop injury was reduced by at least 15 percent. In certain instances, a significant level of reduction of crop injury may be as low as about 10 percent and in other instances no lower than 20 percent. The reduction in level of crop injury is defined as the difference between the observed percentage of crop injury by the thiolcarbamate herbicide without the safening agent and the observed percentage If crop injury by the thiolcarbamate herbicide employed in conjunction with a safening effective amount of an antagonistic agent as defined herein.

Preferred alkyl are aliphatic hydrocarbons having from 1 through 18, inclusive, carbons. The configuration of the structure can be straight-chain, branched-chain, cyclic or a mixed configuration having both branched and cyclic moieties. More preferred alkyl have from 1 through 6, inclusive, carbons.

As employed herein, the terms "lower alkyl" and "lower alkoxy" designate those groups wherein the aliphatic chain is straight or branched and has from 1 through 4 carbons, inclusive.

As employed herein, the term "substituted phenyl" designates phenyl groups of the formula

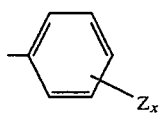

wherein each Z is independently halo, trihalomethyl, hydroxyl, nitro, lower alkyl or lower alkoxy, and x is an integer from 1 through 3, inclusive, provided that no more than two Z's are nitro and that no more than one Z is hydroxyl. The term "halo" designates a halogen atom selected from fluorine, chlorine, bromine and iodine. Preferred halo are chloro and bromo. Preferred trihalomethyl is trifluoromethyl.

Preferred alkenyl have from 2 through 8, inclusive, carbons. More preferred alkenyl have from 3 through 6, inclusive, carbons. Still more preferred alkenyl have 3 carbons and have the unsaturated bond in the 2-position.

Preferred haloalkenyl have from 2 through 8, inclusive, carbons and 1 through 3, inclusive, halogens. More preferred haloalkenyl have from 3 through 6, inclusive, carbons and 1 through 3, inclusive, halogens. Still more preferred haloalkenyl have from 3 through 6, inclusive, carbons and 1 through 3, inclusive, chlorines.

Preferred haloalkynyl have from 2 through 8, inclusive, carbons and 1 through 3, inclusive, halogens. More preferred haloalkynyl have from 3 through 6, inclusive, carbons and 1 through 3, inclusive, halogens. Still more preferred haloalkynyl have from 3 through 6, inclusive, carbons and 1 through 3, inclusive, chlorines.

Preferred substituted alkyl have from 1 through 3, inclusive, substituents selected from the group consisting of acetyl, acetyloxy, lower alkylthio, amino, carbamoyl, dilower alkylcarbamoyl, cyano, hydroxyl, phenyl, substituted phenyl, phenoxyl and substituted phenoxyl, the substituents of which are the same as the substituents of substituted phenyl. More preferred substituted alkyl have, in the aliphatic portion of the group, from 1 through 6, inclusive, carbons. Still more preferred substituted alkyl have one substituent selected from the aforementioned group.

The compounds employed herein as antagonistic agents are either known compounds or are readily prepared from known compounds by old methods known to the skilled chemist.

Thiolcarbamate herbicides are widely known in the art. U.S. Pat. Nos. 3,330,643, 2,913,327, 3,175,897, 3,185,720 and 3,198,786 are but a few of the many patents disclosing thiolcarbamate herbicides which have published in the United States and other countries. Particularly effective safening properties are obtained with selective thiolcarbamates of the formula

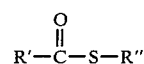

where R' is an organic amino substituent having the nitrogen atom connected directly to the carbon of the

and to two other carbon atoms and where R" represents a non-aromatic unsaturated radical. By non-aromatic is meant that a carbon atom which is part of an aromatic ring is not connected directly to the sulfur. The valences of the amino substituent represented by R' are preferably satisfied by lower alkyl groups but if the chain is interrupted by oxygen or sulfur, compounds having higher molecular weights maintain high biological activity. Moreover, heterocyclic amino substituents are especially efficacious. The unsaturated group represented by R" is preferably an alkenyl group either unsubstituted or substituted by halogen although the presence of halogen serves significantly to support the biological activity. Typical examples of R" comprise cis- and trans-2,3-dichloro-2-butenyl, 3-chloro-2-butenyl, 2-chloroallyl, 2-bromoallyl, 3-chloroallyl, cis- and trans-2,3-dichloroallyl, 3-iodoallyl, 3-iodo-2-butenyl, 2,3-diodo-2-butenyl, 2-fluoro-3-chloroallyl, vinyl, allyl, 2-butenyl, 4-chloro-2-butenyl, 2-iodoallyl, 3-bromoallyl, and 2,3-dibromoallyl.

Particularly good safening of diallate, triallate, vernolate, pebulate, butylate, cycloate, molinate and EPTC herbicides with regard to wheat and sorghum, especially wheat, has been found employing the safening methods and compositions of the present invention.

The method and compositions of this invention are illustrated by the following examples.

EXAMPLES 1 THROUGH 169

The safening effectiveness of representative antagonistic agents on representative thiolcarbamate herbicides with respect to wheat and sorghum is shown by the test results presented in Table I. For each antagonistic agent, there is shown the percent inhibition of the plants by the thiolcarbamate herbicide and the antagonistic agent and the safening effect of the antagonistic agent in terms of reduction of percent inhibition which is determined by subtracting the percent inhibition of the thiolcarbamate herbicide in a specified amount and the antagonistic agent in a specified amount from the percent inhibition of the thiolcarbamate herbicide in the same specified amount but with no antagonistic agent. These results are obtained by the following procedure:

A good grade of top soil is placed in an aluminum pan and compacted to a depth of ⅜ to ½ inch from the top of the pan. A predetermined number of seeds of each of the plant species to be tested are placed on top of the soil in the pans. A quantity of soil sufficient to substantially fill the pan is measured and placed in a suitable container. A measured quantity of the antagonistic agent dispersed or dissolved in a suitable carrier is sprayed on the soil in the container. A measured quantity of the thiolcarbamate herbicide dispersed or dissolved in a suitable carrier is then sprayed on the soil in the container already treated with the safening agent.

The quantity of thiolcarbamate herbicide and antagonistic agent is expressed in terms of kilograms per hectare for ease of comparing the greenhouse test results with field results. The soil containing the antagonistic agent and/or thiolcarbamate herbicide is thoroughly mixed. This mixing is sometimes referred to as incorporation of the herbicide and antagonistic agent into the soil. The mixing or incorporation provides a substantially uniform distribution of the antagonistic agent and herbicide throughout the soil. The seeds are covered with the soil containing the antagonistic agent and thiolcarbamate herbicide and the pans are leveled. The pans are then placed on a sand bench in the greenhouse and watered from below as needed. The plants are observed at the end of approximately 21 days and the results in terms of percent inhibition of each seed lot are recorded. For each test series a pan of plants is also prepared containing no thiolcarbamate herbicide and no antagonistic agent as a control. Additionally, for each test, a pan of plants is prepared with soil covering the seed containing no thiolcarbamate herbicide and only the measured amount of antagonistic agent being incorporated into the soil covering the seeds to ascertain any herbicidal effect of the antagonistic agent alone. For each series of tests the herbicidal effect of the thiolcarbamate herbicide is observed from pans of plants treated with the same quantity of herbicide alone.

In the tables herein, the columns headed Percent Inhibition contain the observations of test pans of plants which quantify the response of plants to a combination treatment of thiolcarbamate herbicide and safening agent. Likewise, the columns headed Safening Effect (%) contain the difference between the response of plants to treatment with thiolcarbamate herbicide and the response of plants to a combination treatment of the same thiolcarbamate herbicide and safening agent.

TABLE I

| Example No. | Amount of triallate Herbicide (kg./ha.) | Antagonistic Agent | Amount (kg./ha.) | Crop | Percent Inhibition | Safening Effect(%) |
| --- | --- | --- | --- | --- | --- | --- |
| 1 | 0.28 | Allylthionocarbanilate | 4.48 | Sorghum | 40 | 55 |
|   | 1.12 | Allylthionocarbanilate | 4.48 | Sorghum | 50 | 49 |
|   | 4.48 | Allylthionocarbanilate | 4.48 | Sorghum | 60 | 38 |
| 2 | 0.28 | Isopropyl-N-butylcarbanilate | 4.48 | Sorghum | 35 | 60 |
|   | 1.12 | Isopropyl-N-butylcarbanilate | 4.48 | Sorghum | 70 | 29 |
| 3 | 0.28 | Allyl-N-methyldithiocarbanilate | 4.48 | Sorghum | 20 | 75 |
|   | 1.12 | Allyl-N-methyldithiocarbanilate | 4.48 | Sorghum | 30 | 69 |
|   | 4.48 | Allyl-N-methyldithiocarbanilate | 4.48 | Sorghum | 65 | 33 |
| 4 | 0.28 | Methyl-N-ethyldithiocarbanilate | 4.48 | Wheat | 10 | 50 |
|   | 0.28 | Methyl-N-ethyldithiocarbanilate | 4.48 | Sorghum | 60 | 35 |
| 5 | 0.14 | 2-chloroallyl-para-ethoxythiolcarbanilate | 4.48 | Sorghum | 40 | 40 |
| 6 | 0.14 | 2-chloroallyl-para-methoxy-thiolcarbanilate | 4.48 | Wheat | 50 | 20 |
| 7 | 0.14 | 2-chloroallyl-N-3-chloro-2-butenyldithiocarbanilate | 4.48 | Wheat | 45 | 25 |
|   | 0.14 | 2-chloroallyl-N-3-chloro-2-butenyldithiocarbanilate | 4.48 | Sorghum | 50 | 30 |
| 8 | 0.14 | Butyl-3,4-dichlorodithiocarbanilate | 4.48 | Wheat | 40 | 30 |
|   | 0.14 | Butyl-3,4-dichlorodithiocarbanilate | 4.48 | Sorghum | 45 | 35 |
| 9 | 0.14 | Tert.butylthiolcarbanilate | 4.48 | Wheat | 25 | 55 |
|   | 0.14 | Tert.butylthiolcarbanilate | 4.48 | Sorghum | 45 | 25 |
|   | 0.56 | Tert.butylthiolcarbanilate | 4.48 | Wheat | 70 | 27 |
|   | 0.56 | Tert.butylthiolcarbanilate | 4.48 | Sorghum | 60 | 34 |
| 10 | 0.14 | Ethyl-meta-methylthiolcarbanilate | 4.48 | Wheat | 20 | 60 |
|   | 0.14 | Ethyl-meta-methylthiolcarbanilate | 4.48 | Sorghum | 40 | 30 |
| 11 | 0.14 | Methyl-meta-methylthiolcarbanilate | 4.48 | Wheat | 20 | 50 |
| 12 | 0.14 | Allyl-N-methyldithiocarbanilate | 4.48 | Wheat | 35 | 25 |
|   | 0.14 | Allyl-N-methyldithiocarbanilate | 4.48 | Sorghum | 20 | 75 |
|   | 0.56 | Allyl-N-methyldithiocarbanilate | 4.48 | Wheat | 80 | 20 |
|   | 0.56 | Allyl-N-methyldithiocarbanilate | 4.48 | Sorghum | 45 | 53 |
| 13 | 0.14 | Methyl-N-ethyldithiocarbanilate | 4.48 | Wheat | 20 | 40 |
|   | 0.14 | Methyl-N-ethyldithiocarbanilate | 4.48 | Sorghum | 45 | 50 |
|   | 0.56 | Methyl-N-ethyldithiocarbanilate | 4.48 | Wheat | 80 | 20 |
|   | 0.56 | Methyl-N-ethyldithiocarbanilate | 4.48 | Sorghum | 65 | 33 |
| 14 | 0.14 | Propyl-N-methylthiol- | 4.48 | Wheat | 0 | 70 |

TABLE I-continued

| Example No. | Amount of triallate Herbicide (kg./ha.) | Antagonistic Agent | Amount (kg./ha.) | Crop | Percent Inhibition | Safening Effect(%) |
|---|---|---|---|---|---|---|
| | 0.14 | Propyl-N-methylthiol-carbanilate | 4.48 | Sorghum | 65 | 20 |
| 15 | 0.14 | Propyl-N-methylthiol-carbanilate | 4.48 | Wheat | 35 | 35 |
| | 0.14 | Propyl-N-methylthiol-carbanilate | 4.48 | Sorghum | 45 | 40 |
| 16 | 0.14 | Butyl-N-methylthiol-carbanilate | 4.48 | Wheat | 0 | 70 |
| | 0.14 | Butyl-N-methylthiol-carbanilate | 4.48 | Sorghum | 40 | 45 |
| | 0.56 | Butyl-N-methylthiol-carbanilate | 4.48 | Sorghum | 60 | 38 |
| 17 | 0.14 | Isobutyl-N-methyl-carbanilate | 4.48 | Wheat | 40 | 30 |
| | 0.14 | Isobutyl-N-methyl-carbanilate | 4.48 | Sorghum | 15 | 70 |
| 18 | 0.14 | Propyl-N-butylthiol-carbanilate | 4.48 | Wheat | 45 | 25 |
| 19 | 0.14 | 2-methylallyl-N-methyl-dithiocarbanilate | 4.48 | Wheat | 0 | 70 |
| | 0.14 | 2-methylallyl-N-methyl-dithiocarbanilate | 4.48 | Sorghum | 25 | 60 |
| | 0.56 | 2-methylallyl-N-methyl-dithiocarbanilate | 4.48 | Sorghum | 55 | 43 |
| 20 | 0.14 | 3-chloroallyl-N-ethyl-dithiocarbanilate | 4.48 | Sorghum | 40 | 45 |
| | 0.56 | 3-chloroallyl-N-ethyl-dithiocarbanilate | 4.48 | Sorghum | 85 | 13 |
| 21 | 0.14 | Allyl-N-ethyldithio-carbanilate | 4.48 | Sorghum | 50 | 35 |
| 22 | 0.14 | 2-propynyl-N-ethyl-dithiocarbanilate | 4.48 | Wheat | 20 | 20 |
| | 0.14 | 2-propynyl-N-ethyl-dithiocarbanilate | 4.48 | Sorghum | 70 | 15 |
| 23 | 0.14 | Butyl-N-ethyldithio-carbanilate | 4.48 | Sorghum | 50 | 35 |
| | 0.56 | Butyl-N-ethyldithio-carbanilate | 4.48 | Sorghum | 75 | 23 |
| 24 | 0.14 | Sec.butyl-N-ethyl-dithiocarbanilate | 4.48 | Sorghum | 10 | 75 |
| | 0.56 | Sec.butyl-N-ethyl-dithiocarbanilate | 4.48 | Sorghum | 30 | 68 |
| 25 | 0.14 | Isobutyl-N-ethyl-dithiocarbanilate | 4.48 | Sorghum | 0 | 85 |
| | 0.56 | Isobutyl-N-ethyl-dithiocarbanilate | 4.48 | Sorghum | 45 | 53 |
| 26 | 0.14 | 2-chloroallyl-N-allyl-3,4-dichlorodithiocarbanilate | 4.48 | Sorghum | 15 | 70 |
| | 0.56 | 2-chloroallyl-N-allyl-3,4-dichlorodithiocarbanilate | 4.48 | Sorghum | 65 | 33 |
| 27 | 0.14 | Methyl-N-allyl-3,4-dichlorodithiocarbanilate | 4.48 | Sorghum | 35 | 50 |
| | 0.56 | Methyl-N-allyl-3,4-dichlorodithiocarbanilate | 4.48 | Sorghum | 70 | 28 |
| 28 | 0.14 | Isopropyl-N-ethyldithio-carbanilate | 4.48 | Sorghum | 10 | 75 |
| | 0.56 | Isopropyl-N-ethyldithio-carbanilate | 4.48 | Sorghum | 75 | 23 |
| 29 | 0.14 | Ethyl-N-ethyldithio-carbanilate | 4.48 | Wheat | 0 | 40 |
| 30 | 0.14 | Allyl-N-ethyldithio-carbanilate | 4.48 | Wheat | 5 | 35 |
| | 0.56 | Allyl-N-ethyldithio-carbanilate | 4.48 | Wheat | 60 | 28 |
| 31 | 0.14 | 2-chloroallyl-para-chloro-N-ethyldithiocarbanilate | 4.48 | Wheat | 25 | 15 |
| 32 | 0.14 | 3-chloropropyl-N-ethyl-thionocarbanilate | 4.48 | Wheat | 20 | 20 |
| 33 | 0.14 | 2-chloroethyl-N-ethyl-thionocarbanilate | 4.48 | Wheat | 25 | 15 |
| 34 | 0.14 | Phenyl-N-methyldithio-carbanilate | 4.48 | Wheat | 15 | 25 |
| 35 | 0.14 | 3-chloroallyl-N-methyl-dithiocarbanilate | 4.48 | Wheat | 20 | 30 |
| | 0.14 | 3-chloroallyl-N-methyl-dithiocarbanilate | 4.48 | Sorghum | 20 | 35 |
| 36 | 0.14 | 3-chloro-2-butenyl-N-methyldithiocarbanilate | 4.48 | Sorghum | 30 | 25 |
| 37 | 0.14 | Cyanomethyl-N-methyl- | 4.48 | Wheat | 10 | 40 |

TABLE I-continued

| Example No. | Amount of triallate Herbicide (kg./ha.) | Antagonistic Agent | Amount (kg./ha.) | Crop | Percent Inhibition | Safening Effect(%) |
|---|---|---|---|---|---|---|
| | | dithiocarbanilate | | | | |
| | 0.14 | Cyanomethyl-N-methyl-dithiocarbanilate | 4.48 | Sorghum | 40 | 15 |
| 38 | 0.14 | Ethyl-N-methyldithio-carbanilate | 4.48 | Wheat | 25 | 25 |
| | 0.14 | Ethyl-N-methyldithio-carbanilate | 4.48 | Sorghum | 0 | 55 |
| | 0.56 | Ethyl-N-methyldithio-carbanilate | 4.48 | Sorghum | 50 | 40 |
| 39 | 0.14 | Propyl-N-methyldithio-carbanilate | 4.48 | Wheat | 25 | 25 |
| | 0.14 | Propyl-N-methyldithio-carbanilate | 4.48 | Sorghum | 0 | 55 |
| | 0.56 | Propyl-N-methyldithio-carbanilate | 4.48 | Sorghum | 30 | 60 |
| 40 | 0.14 | 2-bromoallyl-N-methyl-dithiocarbanilate | 4.48 | Wheat | 25 | 25 |
| | 0.14 | 2-bromoallyl-N-methyl-dithiocarbanilate | 4.48 | Sorghum | 25 | 30 |
| 41 | 0.14 | Carbamoylmethyl-N-methyl-dithiocarbanilate | 4.48 | Sorghum | 20 | 35 |
| 42 | 0.14 | Methyl-N-methylthiol-carbanilate | 4.48 | Sorghum | 10 | 35 |
| 43 | 0.14 | Isopropyl-N-isopropyl-thiolcarbanilate | 4.48 | Sorghum | 25 | 20 |
| 44 | 0.14 | Methyl-N-(2-cyanoethyl)-thiolcarbanilate | 4.48 | Sorghum | 25 | 20 |
| 45 | 0.14 | Allyl-N-isopropylthiol-carbanilate | 4.48 | Sorghum | 15 | 30 |
| 46 | 0.14 | Ethyl-N-(2-carbamoyl-ethyl)thiolcarbanilate | 4.48 | Sorghum | 0 | 45 |
| 47 | 0.14 | Methyl-ortho-fluorothiol-carbanilate | 4.48 | Sorghum | 25 | 20 |
| 48 | 0.14 | Cyclohexylthiolcarbanilate | 4.48 | Wheat | 0 | 20 |
| | 0.14 | Cyclohexylthiolcarbanilate | 4.48 | Sorghum | 20 | 25 |
| | 0.56 | Cyclohexylthiolcarbanilate | 4.48 | Sorghum | 40 | 48 |
| 49 | 0.14 | Methyl-N-methyldithio-carbanilate | 4.48 | Wheat | 0 | 15 |
| | 0.14 | Methyl-N-methyldithio-carbanilate | 4.48 | Sorghum | 15 | 55 |
| 50 | 0.14 | Ethyl-N-methyldithio-carbanilate | 4.48 | Wheat | 0 | 15 |
| 51 | 0.14 | Butyl-N-methyldithio-carbanilate | 4.48 | Wheat | 0 | 15 |
| | 0.14 | Butyl-N-methyldithio-carbanilate | 4.48 | Sorghum | 10 | 60 |
| | 0.56 | Butyl-N-methyldithio-carbanilate | 4.48 | Sorghum | 45 | 53 |
| 52 | 0.14 | Methyl-N-methyl-ortho-methyldithiocarbanilate | 4.48 | Sorghum | 10 | 60 |
| | 0.56 | Methyl-N-methyl-ortho-methyldithiocarbanilate | 4.48 | Sorghum | 75 | 23 |
| 53 | 0.14 | Methyl-N-methyl-para-methyldithiocarbanilate | 4.48 | Wheat | 0 | 15 |
| | 0.14 | Methyl-N-methyl-para-methyldithiocarbanilate | 4.48 | Sorghum | 10 | 60 |
| | 0.56 | Methyl-N-methyl-para-methyldithiocarbanilate | 4.48 | Sorghum | 20 | 78 |
| 54 | 0.14 | Cyclohexyl-meta-methyl-thiolcarbanilate | 4.48 | Sorghum | 40 | 25 |
| 55 | 0.14 | Methyl-2,6-diethyl-thionocarbanilate | 4.48 | Wheat | 25 | 20 |
| 56 | 0.14 | Methyl-para-tert.butyl-thiolcarbanilate | 4.48 | Wheat | 20 | 25 |
| | 0.14 | Methyl-para-tert.butyl-thiolcarbanilate | 4.48 | Sorghum | 15 | 50 |
| 57 | 0.14 | 2-chloroallyl-para-nitrodithiocarbanilate | 4.48 | Wheat | 20 | 25 |
| 58 | 0.14 | Propyl-N-isopropyl-dithiocarbanilate | 4.48 | Wheat | 10 | 35 |
| 59 | 0.14 | Ethyl-N-isopropyl-meta-hydroxythiolcarbanilate | 4.48 | Sorghum | 30 | 35 |
| 60 | 0.14 | Isopropyl-meta-nitro-thionocarbanilate | 4.48 | Wheat | 0 | 45 |
| | 0.14 | Isopropyl-meta-nitro-thionocarbanilate | 4.48 | Sorghum | 25 | 40 |
| 61 | 0.14 | 2-chloroallyl-para-fluorodithiocarbanilate | 4.48 | Wheat | 25 | 20 |
| 62 | 0.14 | Benzyl octamethylene iminecarbothiolate | 4.48 | Wheat | 10 | 20 |

TABLE I-continued

| Example No. | Amount of triallate Herbicide (kg./ha.) | Antagonistic Agent | Amount (kg./ha.) | Crop | Percent Inhibition | Safening Effect(%) |
|---|---|---|---|---|---|---|
| 63 | 0.14 | Meta-trifluoromethylbenzyl-N,N-di-sec.butyldithiocarbamate | 4.48 | Sorghum | 20 | 45 |
|  | 0.56 | Meta-trifluoromethylbenzyl-N,N-di-sec.butyldithiocarbamate | 4.48 | Sorghum | 75 | 20 |
| 64 | 0.14 | 3-cyanobutyl-N,N-di-sec.-butyldithiocarbamate | 4.48 | Sorghum | 30 | 35 |
| 65 | 0.14 | Carbamoylmethyl-N,N-di-sec.butylthiolcarbamate | 4.48 | Sorghum | 20 | 45 |
| 66 | 0.14 | Para-fluorobenzyl-N-methyl-dithiocarbanilate | 4.48 | Wheat | 35 | 35 |
| 67 | 0.28 | Cyanomethyl-N-ethyl-dithiocarbanilate | 4.48 | Wheat | 35 | 35 |
| 68 | 0.28 | Ethyl-N-propyldithio-carbanilate | 4.48 | Sorghum | 65 | 25 |
| 69 | 0.28 | Butyl-N-propyldithio-carbanilate | 4.48 | Sorghum | 70 | 20 |
| 70 | 0.28 | Hexyl-N-propylthiol-carbanilate | 4.48 | Sorghum | 35 | 55 |
| 71 | 0.28 | 2-cyanoethyl-N-ethyl-dithiocarbanilate | 4.48 | Wheat | 50 | 20 |
|  | 0.28 | 2-cyanoethyl-N-ethyl-dithiocarbanilate | 4.48 | Sorghum | 0 | 90 |
|  | 0.56 | 2-cyanoethyl-N-ethyl-dithiocarbanilate | 4.48 | Sorghum | 10 | 88 |
| 72 | 0.28 | Methyl-2-tert.butyl-6-methylthiolcarbanilate | 2.24 | Wheat | 60 | 25 |
| 73 | 0.28 | Methyl-3-chloro-6-methyl-thionocarbanilate | 2.24 | Wheat | 60 | 25 |
| 74 | 0.28 | Methyl-N-butylthiol-carbanilate | 2.24 | Wheat | 65 | 20 |
| 75 | 0.28 | Methyl-N-butyldithio-carbanilate | 2.24 | Wheat | 60 | 25 |
| 76 | 0.28 | 2-cyclohexen-1-yl-methyldithiocarbamate | 2.24 | Wheat | 55 | 15 |
| 77 | 0.28 | 2-cyclohexen-1-yl-methyl-dithiocarbamate | 4.48 | Wheat | 55 | 15 |
| 78 | 0.28 | 2-cyclohexen-1-yl-(3-ethoxypropyl)-dithio-carbamate | 4.48 | Sorghum | 35 | 20 |
| 79 | 0.28 | 2-cyclohexen-1-yl-diiso-propylthiolcarbamate | 4.48 | Sorghum | 30 | 25 |
| 80 | 0.28 | Methyl-3,6-dihydro-1(2H)-pyridinecarbonthiolate | 4.48 | Sorghum | 35 | 20 |
| 81 | 0.28 | Allyl-3,6-dihydro-1(2H)-pyridinecarbothiolate | 4.48 | Sorghum | 35 | 20 |
| 82 | 0.28 | Isopropyl-piperidinethiono-carboxylate | 2.24 | Wheat | 55 | 15 |
| 83 | 0.28 | Butyl-3,6-dihydro-1(2H)-pyridinecarbothiolate | 1.12 | Sorghum | 35 | 20 |
| 84 | 0.28 | Isopropyl-N-methyl-1-cyclohexene-1-carbamate | 4.48 | Wheat | 50 | 20 |
| 85 | 0.28 | Ethyl-N-(1-cyclohexen-1-yl)-N-methylthiolcarbamate | 4.48 | Wheat | 55 | 15 |
| 86 | 0.28 | Butyl-N-(1-cyclohexen-1-yl)-N-methylthiolcarbamate | 2.24 | Wheat | 55 | 15 |
|  | 0.28 | Butyl-N-(1-cyclohexen-1-yl)-N-methylthiolcarbamate | 2.24 | Sorghum | 30 | 25 |
| 87 | 0.28 | Ethyl-N-(1-cyclohexen-1-yl)-N-isopropylthiolcarbamate | 5.60 | Wheat | 45 | 25 |
| 88 | 0.28 | Butyl thiolcarbamate | 4.48 | Sorghum | 25 | 30 |
| 89 | 0.28 | Methyl-N-isopropylthiono-carbanilate | 4.48 | Wheat | 20 | 38 |
|  | 0.28 | Methyl-N-isopropylthiono-carbanilate | 4.48 | Sorghum | 45 | 40 |
| 90 | 0.28 | Acetylmethyl-N-ethyldithio-carbanilate | 4.48 | Wheat | 35 | 23 |
|  | 0.28 | Acetylmethyl-N-ethyldithio-carbanilate | 4.48 | Sorghum | 55 | 30 |
| 91 | 0.28 | Ortho-fluorobenzyl-N-ethyl-dithiocarbanilate | 4.48 | Wheat | 35 | 23 |
|  | 0.28 | Ortho-fluorobenzyl-N-ethyl-dithiocarbanilate | 4.48 | Sorghum | 15 | 70 |
| 92 | 0.28 | Propyl-N-propylcarbanilate | 4.48 | Wheat | 25 | 33 |
|  | 0.28 | Propyl-N-propylcarbanilate | 4.48 | Sorghum | 40 | 45 |
| 93 | 0.28 | Butyl-N-propylcarbanilate | 4.48 | Wheat | 20 | 38 |
|  | 0.28 | Butyl-N-propylcarbanilate | 4.48 | Sorghum | 0 | 85 |
| 94 | 0.28 | Phenyl-N-propylcarbanilate | 4.48 | Wheat | 10 | 48 |
|  | 0.28 | Phenyl-N-propylcarbanilate | 4.48 | Sorghum | 65 | 20 |
| 95 | 0.28 | Methyl-N-methyl-para-chlorodithiocarbanilate | 4.48 | Wheat | 30 | 28 |

TABLE I-continued

| Example No. | Amount of triallate Herbicide (kg./ha.) | Antagonistic Agent | Amount (kg./ha.) | Crop | Percent Inhibition | Safening Effect(%) |
|---|---|---|---|---|---|---|
| | 0.28 | Methyl-N-methyl-para-chlorodithiocarbanilate | 4.48 | Sorghum | 0 | 85 |
| 96 | 0.28 | Benzyldithiocarbamate | 4.48 | Sorghum | 60 | 30 |
| 97 | 0.28 | Tert.butyldiisopropyl-dithiocarbamate | 4.48 | Wheat | 30 | 25 |
| 98 | 0.28 | 3-chloropropylmethylthiol-carbamate | 4.48 | Sorghum | 55 | 35 |
| 99 | 0.28 | Butyl-N-benzyl-N-methyl-dithiocarbamate | 4.48 | Wheat | 20 | 35 |
| 100 | 0.28 | Methyl-N-benzyl-N-methyldithiocarbamate | 4.48 | Wheat | 35 | 20 |
| | 0.28 | Methyl-N-benzyl-N-methyldithiocarbamate | 4.48 | Sorghum | 30 | 60 |
| 101 | 0.28 | Phenyldiethyldithio-carbamate | 4.48 | Wheat | 45 | 25 |
| 102 | 0.28 | 2-chloroethyl-4-morpholinecarbothionate | 4.48 | Wheat | 50 | 20 |
| 103 | 0.28 | 2-chloroallyl-2,6-dimethyl-4-morpholinecarbothionate | 4.48 | Wheat | 50 | 20 |
| 104 | 0.28 | Hexylhexahydro-1H-azepine-1-carbothiolate | 4.48 | Wheat | 50 | 20 |
| 105 | 0.28 | Ethylthiolcyclohexane-carbamate | 4.48 | Wheat | 45 | 35 |
| | 0.28 | Ethylthiolcyclohexane-carbamate | 4.48 | Sorghum | 70 | 15 |
| 106 | 0.28 | Methyl-N-butyldithiocyclo-hexanecarbamate | 4.48 | Wheat | 30 | 50 |
| | 0.28 | Methyl-N-butyldithiocyclo-hexanecarbamate | 4.48 | Sorghum | 35 | 50 |
| 107 | 0.28 | Methyl-N-methylthiono-cyclohexanecarbamate | 4.48 | Wheat | 20 | 60 |
| 108 | 0.28 | Ethyl-N-methylthionocyclo-hexanecarbamate | 4.48 | Wheat | 50 | 30 |
| | 0.28 | Ethyl-N-methylthionocyclo-hexanecarbamate | 4.48 | Sorghum | 40 | 45 |
| 109 | 0.28 | Ethyl-N-ethylthionocyclo-hexanecarbamate | 4.48 | Wheat | 50 | 30 |
| | 0.28 | Ethyl-N-ethylthionocyclo-hexanecarbamate | 4.48 | Sorghum | 45 | 40 |
| 110 | 0.28 | Methyl-N-butylthiono-cyclohexanecarbamate | 4.48 | Wheat | 50 | 30 |
| 111 | 0.28 | 2-propynyl-2,5-dimethyl-pyrrolidinethiocarboxylate | 4.48 | Wheat | 60 | 20 |
| 112 | 0.28 | 2-chloroallyl-meta-methyl-dithiocarbanilate | 4.48 | Wheat | 75 | 15 |
| 113 | 0.28 | Propyl-N-butylthiono-cyclohexanecarbamate | 4.48 | Wheat | 65 | 25 |
| 114 | 0.28 | Methyl-N-benzyl-N-isopropyldithiocarbamate | 4.48 | Wheat | 75 | 15 |
| | 0.28 | Methyl-N-benzyl-N-isopropyldithiocarbamate | 4.48 | Sorghum | 30 | 65 |
| 115 | 0.28 | Ethyl-N-benzyl-N-iso-propyldithiocarbamate | 4.48 | Sorghum | 70 | 25 |
| 116 | 0.28 | Methyl-N-benzyl-N-iso-propylthiolcarbamate | 4.48 | Wheat | 70 | 20 |
| 117 | 0.28 | Ethyl-octahydro-1H-azonine-thionocarboxylate | 4.48 | Wheat | 75 | 15 |
| | 0.28 | Ethyl-octahydro-1H-azonine-thionocarboxylate | 4.48 | Sorghum | 50 | 45 |
| 118 | 0.14 | Methyl-N-butylthiol-carbanilate | 4.48 | Wheat | 25 | 23 |
| | 0.28 | Methyl-N-butylthiol-carbanilate | 4.48 | Wheat | 35 | 25 |
| | 0.14 | Methyl-N-butylthiol-carbanilate | 4.48 | Sorghum | 45 | 20 |
| 119 | 0.14 | Methyl-N-butyldithio-carbanilate | 4.48 | Wheat | 10 | 38 |
| | 0.28 | Methyl-N-butyldithio-carbanilate | 4.48 | Wheat | 35 | 25 |
| | 0.14 | Methyl-N-butyldithio-carbanilate | 4.48 | Sorghum | 20 | 45 |
| | 0.28 | Methyl-N-butyldithio-carbanilate | 4.48 | Sorghum | 60 | 28 |
| 120 | 0.14 | Para-fluorobenzyl-N-methyldithiocarbanilate | 4.48 | Wheat | 15 | 33 |
| | 0.28 | Para-fluorobenzyl-N-methyldithiocarbanilate | 4.48 | Wheat | 45 | 15 |
| 121 | 0.14 | Cyanomethyl-N-ethyldithio-carbanilate | 4.48 | Wheat | 30 | 18 |
| | 0.28 | Cyanomethyl-N-ethyldithio- | 4.48 | Wheat | 30 | 30 |

TABLE I-continued

| Example No. | Amount of triallate Herbicide (kg./ha.) | Antagonistic Agent | Amount (kg./ha.) | Crop | Percent Inhibition | Safening Effect(%) |
|---|---|---|---|---|---|---|
| 122 | 0.14 | Methyl-N-isopropylthiono-carbanilate | 4.48 | Wheat | 15 | 33 |
|  | 0.28 | Methyl-N-isopropylthiono-carbanilate | 4.48 | Wheat | 25 | 35 |
|  | 0.14 | Methyl-N-isopropylthiono-carbanilate | 4.48 | Sorghum | 35 | 30 |
| 123 | 0.14 | Methyl-N-methylpara-chloro-dithiocarbanilate | 4.48 | Sorghum | 15 | 50 |
|  | 0.28 | Methyl-N-methylpara-chloro-dithiocarbanilate | 4.48 | Sorghum | 10 | 78 |
|  | 0.56 | Methyl-N-methylpara-chloro-dithiocarbanilate | 4.48 | Sorghum | 25 | 75 |
|  | 1.12 | Methyl-N-methylpara-chloro-dithiocarbanilate | 4.48 | Sorghum | 35 | 60 |
| 124 | 0.28 | Ethyl-N-(alpha-methyl-benzyl)dithiocarbamate | 4.48 | Sorghum | 20 | 20 |
| 125 | 0.28 | 2,3,3-trichlorochlorallyl-N-(alpha-methylbenzyl)-dithiocarbamate | 2.24 | Wheat | 20 | 35 |
| 126 | 0.28 | Propyl-N-(alpha-methyl-benzyl)-dithiocarbamate | 8.96 | Sorghum | 15 | 25 |
| 127 | 0.28 | Methyl-N-(alpha-methyl-benzyl)carbamate | 8.96 | Sorghum | 25 | 15 |
| 128 | 0.28 | Ortho-fluorobenzyl-N-(alpha-methylbenzyl)thiol-carbamate | 4.48 | Sorghum | 20 | 20 |
| 129 | 0.28 | 2-bromoallyl-N-(alpha-methylbenzyl)thiolcarbamate | 4.48 | Sorghum | 15 | 25 |
| 130 | 0.28 | 2-chloroallyl-N-(alpha-methylbenzyl)thiolcarbamate | 4.48 | Wheat | 30 | 25 |
|  | 0.28 | 2-chloroallyl-N-(alpha-methylbenzyl)thiolcarbamate | 4.48 | Sorghum | 10 | 30 |
| 131 | 0.28 | 3-chloropropyldimethyl-dithiocarbamate | 2.24 | Wheat | 40 | 35 |
|  | 0.28 | 3-chloropropyldimethyl-dithiocarbamate | 2.24 | Sorghum | 40 | 20 |
| 132 | 0.28 | 2,3,3-trichloroallyl-diethyldithiocarbamate | 1.12 | Sorghum | 30 | 30 |
| 133 | 0.28 | 3,3-dichloroallylthiol-carbamate | 8.96 | Sorghum | 35 | 25 |
| 134 | 0.28 | Tert.butyl(2-methylallyl)-2-propynylthiolcarbamate | 0.56 | Wheat | 50 | 20 |
| 135 | 0.28 | 2-(methylthio)ethyl-N-ethyldithiocarbanilate | 4.48 | Sorghum | 20 | 70 |
| 136 | 0.28 | 2,4-dichlorophenyl-N-methylcarbanilate | 4.48 | Sorghum | 35 | 35 |
| 137 | 0.28 | Para-methoxyphenyl-N-ethylthionocarbanilate | 4.48 | Wheat | 50 | 25 |
|  | 0.28 | Para-methoxyphenyl-N-ethylthionocarbanilate | 4.48 | Sorghum | 35 | 35 |
| 138 | 0.28 | Para-methoxyphenyl-N-methylthionocarbanilate | 2.24 | Sorghum | 50 | 20 |
| 139 | 0.28 | Methyl-N-ethyl-para-chlorodithiocarbanilate | 4.48 | Sorghum | 25 | 28 |
| 140 | 0.28 | 2-(methylthio)ethyl-N-methyldithiocarbanilate | 4.48 | Sorghum | 30 | 55 |
|  | 0.56 | 2-(methylthio)ethyl-N-methyldithiocarbanilate | 4.48 | Sorghum | 40 | 58 |
| 141 | 0.28 | Ortho-fluorobenzyl-N-methyldithiocarbanilate | 4.48 | Sorghum | 50 | 35 |
| 142 | 0.28 | Meta-fluorobenzyl-N-methyldithiocarbanilate | 4.48 | Sorghum | 65 | 20 |
| 143 | 0.28 | Para-chlorophenoxymethyl-N-methyldithiocarbanilate | 4.48 | Sorghum | 40 | 45 |
| 144 | 0.28 | Cyanomethyl-N-ethyl-dithiocarbanilate | 4.48 | Sorghum | 30 | 50 |
|  | 0.56 | Cyanomethyl-N-ethyl-dithiocarbanilate | 4.48 | Sorghum | 45 | 53 |
| 145 | 0.28 | Meta-trifluoromethylbenzyl-N-methyldithiocarbanilate | 4.48 | Sorghum | 65 | 25 |
| 146 | 0.28 | Methyl-N-propyldithio-carbanilate | 4.48 | Sorghum | 75 | 15 |
| 147 | 0.14 | Allylthionocarbanilate | 4.48 | Sorghum | 50 | 25 |
| 148 | 0.14 | Cyanoethyl-N-methyl-dithiocarbanilate | 4.48 | Sorghum | 15 | 60 |
| 149 | 0.14 | Butyl-N-isopropyldithio-carbanilate | 4.48 | Sorghum | 35 | 40 |
| 150 | 0.14 | Butyl-N-isopropyl-carbanilate | 4.48 | Sorghum | 10 | 65 |

TABLE I-continued

| Example No. | Amount of triallate Herbicide (kg./ha.) | Antagonistic Agent | Amount (kg./ha.) | Crop | Percent Inhibition | Safening Effect(%) |
|---|---|---|---|---|---|---|
| | 0.56 | Butyl-N-isopropyl-carbanilate | 4.48 | Sorghum | 20 | 78 |
| 151 | 0.14 | Allylthionocarbanilate | 4.48 | Sorghum | 10 | 50 |
| | 0.56 | Allylthionocarbanilate | 4.48 | Sorghum | 65 | 28 |
| 152 | 0.14 | Butylthiolcarbanilate | 4.48 | Sorghum | 25 | 35 |
| 153 | 0.14 | 2-dimethylaminoethyl-N-methyldithiocarbanilate | 4.48 | Sorghum | 45 | 15 |
| 154 | 0.14 | Allyl-meta-chlorodithio-carbanilate | 4.48 | Sorghum | 45 | 15 |
| | 0.56 | Allyl-meta-chlorodithio-carbanilate | 4.48 | Sorghum | 80 | 13 |
| 155 | 0.14 | Methylthionocarbanilate | 4.48 | Sorghum | 35 | 25 |
| | 0.56 | Methylthionocarbanilate | 4.48 | Sorghum | 75 | 18 |
| 156 | 0.14 | 2-chloroallyldithio-carbanilate | 4.48 | Sorghum | 25 | 35 |
| | 0.56 | 2-chloroallyldithio-carbanilate | 4.48 | Sorghum | 80 | 13 |
| 157 | 0.14 | 2-chloroallyl-N-propyl-dithiocarbanilate | 4.48 | Sorghum | 35 | 25 |
| 158 | 0.14 | Tert.butylthiocarbanilate | 4.48 | Wheat | 10 | 20 |
| | 0.14 | Tert.butylthiocarbanilate | 4.48 | Sorghum | 30 | 25 |
| | 0.28 | Tert.butylthiocarbanilate | 4.48 | Sorghum | 30 | 50 |
| 159 | 0.14 | Propyl-N-methylthiol-carbanilate | 4.48 | Sorghum | 40 | 15 |
| | 0.28 | Propyl-N-methylthiol-carbanilate | 4.48 | Sorghum | 65 | 15 |
| | 0.56 | Propyl-N-methylthiol-carbanilate | 4.48 | Sorghum | 80 | 18 |
| 160 | 0.14 | Butyl-N-methylthiol-carbanilate | 4.48 | Sorghum | 25 | 30 |
| | 0.28 | Butyl-N-methylthiol-carbanilate | 4.48 | Sorghum | 20 | 60 |
| | 0.56 | Butyl-N-methylthiol-carbanilate | 4.48 | Sorghum | 35 | 63 |
| 161 | 0.14 | 2-methylallyl-N-methyl-dithiocarbanilate | 4.48 | Sorghum | 20 | 35 |
| | 0.28 | 2-methylallyl-N-methyl-dithiocarbanilate | 4.48 | Sorghum | 40 | 40 |
| | 0.56 | 2-methylallyl-N-methyl-dithiocarbanilate | 4.48 | Sorghum | 60 | 38 |
| 162 | 0.07 | Allyl-N-ethylthiono-carbanilate | 4.48 | Wheat | 0 | 10 |
| | 0.14 | Allyl-N-ethylthiono-carbanilate | 4.48 | Wheat | 10 | 20 |
| | 0.28 | Allyl-N-ethylthiono-carbanilate | 4.48 | Wheat | 50 | 25 |
| 163 | 0.14 | Phenyl-N-methyldithio-carbanilate | 4.48 | Sorghum | 35 | 20 |
| 164 | 0.07 | Cyanomethyl-N-methyl-dithiocarbanilate | 4.48 | Sorghum | 0 | 15 |
| | 0.14 | Cyanomethyl-N-methyl-dithiocarbanilate | 4.48 | Sorghum | 15 | 40 |
| | 0.28 | Cyanomethyl-N-methyl-dithiocarbanilate | 4.48 | Sorghum | 45 | 35 |
| | 0.56 | Cyanomethyl-N-methyl-dithiocarbanilate | 4.48 | Sorghum | 65 | 33 |
| 165 | 0.14 | Hexylhexahydro(1H)-azepine-1-carbothiolate | 1.12 | Wheat | 35 | 35 |
| 166 | 0.14 | Methyl-N-butyldithio-cyclohexanecarbamate | 2.24 | Wheat | 25 | 45 |
| 167 | 0.14 | Butyl-N-benzyl-N-methyl-dithiocarbamate | 1.12 | Wheat | 50 | 20 |
| 168 | 0.14 | 2,3,3-trichloroallyl-N-alpha-methylbenzyldithio-carbamic acid | 2.24 | Wheat | 0 | 50 |
| | 0.28 | 2,3,3-trichloroallyl-N-alpha-methylbenzyldithio-carbamic acid | 2.24 | Wheat | 40 | 20 |
| 169 | 0.14 | 2-chloroallyl-N-alpha-methylbenzylthiolcarbamate | 4.48 | Wheat | 25 | 25 |
| | 0.14 | 2-chloroallyl-N-alpha-methylbenzylthiolcarbamate | 4.48 | Sorghum | 25 | 50 |
| | 0.28 | 2-chloroallyl-N-alpha-methylbenzylthiolcarbamate | 4.48 | Sorghum | 60 | 35 |

Although in the foregoing examples the safening agent is applied to the soil before the thiolcarbamate herbicide, equivalent results are obtainable when the safening agent is applied in mixture with the thiolcarbamate herbicide or in sequence after the thiolcarbamate herbicide is applied. This also is observed in post-emergent applications. The ability to be applied as mixtures and obtain safening of thiolcarbamate herbicide with wheat and sorghum is confirmed in tank mix tests.

A key contribution of the present invention is that the safening or antagonistic agents when applied to seed reduce crop injury without reducing effective weed control by the thiolcarbamate herbicides.

EXAMPLES 170 to 180

The procedure of Examples 1 to 169 is repeated except that the antagonistic agent is applied as a seed treatment rather than as a sequential spray before application of the herbicide. For seed treatment, the antagonistic agent is mixed with an inert carrier comprising a finely-divided clay and a high surface area calcium silicate in a range of weight percentages of active antagonistic agent to inert carrier. An excess of the antagonistic agent/inert carrier mixture is thoroughly mixed with the crop seed to be protected. With respect to wheat seed, the following correlation of the composition of the mixture to the quantity of active ingredient per unit weight of wheat seed is observed.

| Percent by weight of active antagonistic agent to inert carrier (% composition) | Percent by weight of active antagonistic agent to wheat seed after treatment (% on seed) |
|---|---|
| 1.25 | 0.125 |
| 2.5 | 0.25 |
| 5 | 0.5 |
| 10 | 1.0 |

In a similar fashion, the active safening agent is sometimes dissolved or dispersed in one or more organic liquids. The solution or dispersion is mixed with the seed in a proportion to give the appropriate amount of active agent on the seed, as measured by weight, after the carrier liquid has been evaporated off.

The results of applying antagonistic agents as a seed treatment to wheat seed at various percentages by weight and applying triallate herbicide as a pre-emergent herbicide at various application rates is shown in Table II(A). Good control of weed species is observed.

TABLE II (A)

| Example No. | Amount of triallate Herbicide (kg./ha.) | Antagonistic Agent | Weight % On Seed Of Antagonistic Agent | Percent Inhibition Of Wheat | Safening Effect (%) |
|---|---|---|---|---|---|
| 170 | 0.035 | Methyl-N-ethyldithiocarbanilate | 0.0156 | 0 | 20 |
|  | 0.035 | Methyl-N-ethyldithiocarbanilate | 0.0312 | 0 | 20 |
|  | 0.035 | Methyl-N-ethyldithiocarbanilate | 0.0625 | 0 | 20 |
|  | 0.035 | Methyl-N-ethyldithiocarbanilate | 0.125 | 0 | 20 |
|  | 0.035 | Methyl-N-ethyldithiocarbanilate | 0.25 | 0 | 20 |
|  | 0.07 | Methyl-N-ethyldithiocarbanilate | 0.0156 | 50 | 0 |
|  | 0.07 | Methyl-N-ethyldithiocarbanilate | 0.0312 | 40 | 10 |
|  | 0.07 | Methyl-N-ethyldithiocarbanilate | 0.0625 | 15 | 35 |
|  | 0.07 | Methyl-N-ethyldithiocarbanilate | 0.125 | 10 | 40 |
|  | 0.07 | Methyl-N-ethyldithiocarbanilate | 0.25 | 5 | 45 |
|  | 0.14 | Methyl-N-ethyldithiocarbanilate | 0.0156 | 70 | 10 |
|  | 0.14 | Methyl-N-ethyldithiocarbanilate | 0.0312 | 70 | 10 |
|  | 0.14 | Methyl-N-ethyldithiocarbanilate | 0.0625 | 45 | 35 |
|  | 0.14 | Methyl-N-ethyldithiocarbanilate | 0.125 | 10 | 70 |
|  | 0.14 | Methyl-N-ethyldithiocarbanilate | 0.25 | 0 | 80 |
|  | 0.28 | Methyl-N-ethyldithiocarbanilate | 0.0156 | 85 | 10 |
|  | 0.28 | Methyl-N-ethyldithiocarbanilate | 0.0312 | 90 | 5 |
|  | 0.28 | Methyl-N-ethyldithiocarbanilate | 0.0625 | 85 | 10 |
|  | 0.28 | Methyl-N-ethyldithiocarbanilate | 0.125 | 50 | 45 |
|  | 0.28 | Methyl-N-ethyldithiocarbanilate | 0.25 | 10 | 85 |
|  | 0.56 | Methyl-N-ethyldithiocarbanilate | 0.0156 | 99 | 1 |
|  | 0.56 | Methyl-N-ethyldithiocarbanilate | 0.0312 | 90 | 10 |
|  | 0.56 | Methyl-N-ethyldithiocarbanilate | 0.0625 | 90 | 10 |
|  | 0.56 | Methyl-N-ethyldithiocarbanilate | 0.125 | 80 | 20 |
|  | 0.56 | Methyl-N-ethyldithiocarbanilate | 0.25 | 60 | 40 |

TABLE II (A)-continued

| Example No. | Amount of triallate Herbicide (kg./ha.) | Antagonistic Agent | Weight % On Seed Of Antagonistic Agent | Percent Inhibition Of Wheat | Safening Effect (%) |
|---|---|---|---|---|---|
| | 1.12 | Methyl-N-ethyldithio-carbanilate | 0.0156 | 100 | 0 |
| | 1.12 | Methyl-N-ethyldithio-carbanilate | 0.0312 | 95 | 5 |
| | 1.12 | Methyl-N-ethyldithio-carbanilate | 0.0625 | 95 | 5 |
| | 1.12 | Methyl-N-ethyldithio-carbanilate | 0.125 | 95 | 5 |
| | 1.12 | Methyl-N-ethyldithio-carbanilate | 0.25 | 85 | 15 |
| 171 | 0.28 | Ethyloctahydro-1H-azonine-thionocarboxylate | 0.125 | 50 | 10 |
| | 0.28 | Ethyloctahydro-1H-azonine-thionocarboxylate | 0.25 | 40 | 20 |
| | 0.56 | Ethyloctahydro-1H-azonine-thionocarboxylate | 0.125 | 80 | 10 |
| | 0.56 | Ethyloctahydro-1H-azonine-thionocarboxylate | 0.25 | 50 | 40 |
| 172 | 0.14 | Benzylisobutyldithiocarbamate | 0.50 | 40 | 20 |
| | 0.28 | Benzylisobutyldithiocarbamate | 0.50 | 35 | 40 |
| | 0.56 | Benzylisobutyldithiocarbamate | 0.50 | 60 | 25 |
| | 1.12 | Benzylisobutyldithiocarbamate | 0.50 | 65 | 33 |
| 173 | 0.28 | Methyl-N-methyldithio-carbanilate | 0.125 | 20 | 55 |
| | 0.28 | Methyl-N-methyldithio carbanilate | 0.5 | 0 | 75 |
| | 0.56 | Methyl-N-methyldithio-carbanilate | 0.125 | 55 | 40 |
| | 0.56 | Methyl-N-methyldithio-carbanilate | 0.5 | 5 | 90 |
| | 1.12 | Methyl-N-methyldithio-carbanilate | 0.125 | 80 | 10 |
| | 1.12 | Methyl-N-methyldithio carbanilate | 0.5 | 5 | 90 |
| 174 | 0.14 | Methyl-N-methyldithio-carbanilate | 0.063 | 13 | 20 |
| | 0.14 | Methyl-N-methyldithio-carbanilate | 0.125 | 18 | 15 |
| | 0.14 | Methyl-N-methyldithio-carbanilate | 0.25 | 10 | 23 |
| | 0.14 | Methyl-N-methyldithio-carbanilate | 0.5 | 15 | 18 |
| | 0.14 | Methyl-N-methyldithio-carbanilate | 1.0 | 5 | 28 |
| | 0.28 | Methyl-N-methyldithio-carbanilate | 0.063 | 45 | 30 |
| | 0.28 | Methyl-N-methyldithio-carbanilate | 0.125 | 15 | 60 |
| | 0.28 | Methyl-N-methyldithio-carbanilate | 0.25 | 10 | 65 |
| | 0.28 | Methyl-N-methyldithio-carbanilate | 0.5 | 10 | 65 |
| | 0.28 | Methyl-N-methyldithio-carbanilate | 1.0 | 10 | 65 |
| | 0.56 | Methyl-N-methyldithio-carbanilate | 0.125 | 68 | 17 |
| | 0.56 | Methyl-N-methyldithio-carbanilate | 0.25 | 45 | 40 |
| | 0.56 | Methyl-N-methyldithio-carbanilate | 0.5 | 13 | 72 |
| | 0.56 | Methyl-N-methyldithio-carbanilate | 1.0 | 15 | 70 |
| | 1.12 | Methyl-N-methyldithio-carbanilate | 0.125 | 88 | 11 |
| | 1.12 | Methyl-N-methyldithio-carbanilate | 0.25 | 73 | 26 |
| | 1.12 | Methyl-N-methyldithio-carbanilate | 0.5 | 43 | 56 |
| | 1.12 | Methyl-N-methyldithio-carbanilate | 1.0 | 13 | 86 |
| | 2.24 | Methyl-N-methyldithio-carbanilate | 0.125 | 92 | 7 |
| | 2.24 | Methyl-N-methyldithio-carbanilate | 0.25 | 80 | 19 |
| | 2.24 | Methyl-N-methyldithio-carbanilate | 0.5 | 48 | 51 |
| | 2.24 | Methyl-N-methyldithio-carbanilate | 1.0 | 20 | 79 |
| 175 | 0.14 | Tert. butylthiolcarbanilate | 0.031 | 10 | 10 |

TABLE II (A)-continued

| Example No. | Amount of triallate Herbicide (kg./ha.) | Antagonistic Agent | Weight % On Seed Of Antagonistic Agent | Percent Inhibition Of Wheat | Safening Effect (%) |
|---|---|---|---|---|---|
| | 0.14 | Tert. butylthiolcarbanilate | 0.125 | 0 | 20 |
| | 0.14 | Tert. butylthiolcarbanilate | 0.50 | 0 | 20 |
| | 0.28 | Tert. butylthiolcarbanilate | 0.031 | 0 | 40 |
| | 0.28 | Tert. butylthiolcarbanilate | 0.125 | 0 | 40 |
| | 0.28 | Tert. butylthiolcarbanilate | 0.5 | 0 | 40 |
| | 0.56 | Tert. butylthiolcarbanilate | 0.031 | 50 | 45 |
| | 0.56 | Tert. butylthiolcarbanilate | 0.125 | 50 | 45 |
| | 0.56 | Tert. butylthiolcarbanilate | 0.5 | 45 | 50 |
| | 1.12 | Tert. butylthiolcarbanilate | 0.125 | 80 | 15 |
| | 1.12 | Tert. butylthiolcarbanilate | 0.5 | 70 | 25 |
| | 2.24 | Tert. butylthiolcarbanilate | 0.125 | 90 | 5 |
| | 2.24 | Tert. butylthiolcarbanilate | 0.5 | 70 | 25 |
| 176 | 0.28 | Allyl-N-ethylthionocarbanilate | 0.031 | 10 | 40 |
| | 0.28 | Allyl-N-ethylthionocarbanilate | 0.125 | 10 | 40 |
| | 0.28 | Allyl-N-ethylthionocarbanilate | 0.5 | 25 | 25 |
| | 0.56 | Allyl-N-ethylthionocarbanilate | 0.031 | 70 | 10 |
| | 0.56 | Allyl-N-ethylthionocarbanilate | 0.125 | 35 | 45 |
| | 0.56 | Allyl-N-ethylthionocarbanilate | 0.5 | 30 | 50 |
| | 1.12 | Ally-N-ethylthionocarbanilate | 0.031 | 85 | 15 |
| | 1.12 | Allyl-N-ethylthionocarbanilate | 0.125 | 75 | 25 |
| | 1.12 | Allyl-N-ethylthionocarbanilate | 0.5 | 25 | 75 |
| | 2.24 | Allyl-N-ethylthionocarbanilate | 0.125 | 7 | 30 |
| | 2.24 | Allyl-N-ethylthionocarbanilate | 0.5 | 90 | 10 |
| 177 | 0.14 | Methyl-N-isopropylthionocarbanilate | 0.031 | 20 | 20 |
| | 0.14 | Methyl-N-isopropylthionocarbanilate | 0.125 | 15 | 25 |
| | 0.14 | Methyl-N-isopropylthionocarbanilate | 0.5 | 20 | 20 |
| 178 | 0.28 | Methyl-N-butylthiolcarbanilate | 0.031 | 30 | 40 |
| | 0.28 | Methyl-N-butylthiolcarbanilate | 0.125 | 25 | 45 |
| | 0.28 | Methyl-N-butylthiolcarbanilate | 0.50 | 40 | 30 |
| | 0.56 | Methyl-N-butylthiolcarbanilate | 0.031 | 85 | 10 |
| | 0.56 | Methyl-N-butylthiolcarbanilate | 0.125 | 35 | 60 |
| | 0.56 | Methyl-N-butylthiolcarbanilate | 0.5 | 35 | 60 |
| 179 | 0.14 | 2,3,3-trichloroallyl-N-(alpha-methylbenzyl)dithiocarbamate | 0.031 | 0 | 20 |
| | 0.14 | 2,3,3-trichloroallyl-N-(alpha-methylbenzyl)dithiocarbamate | 0.125 | 0 | 20 |
| | 0.14 | 2,3,3-trichloroallyl-N-(alpha-methylbenzyl)dithiocarbamate | 0.5 | 15 | 5 |
| | 0.28 | 2,3,3-trichloroallyl-N-(alpha-methylbenzyl)dithiocarbamate | 0.031 | 0 | 50 |
| | 0.28 | 2,3,3-trichloroallyl-N-(alpha-methylbenzyl)dithiocarbamate | 0.125 | 0 | 50 |
| | 0.28 | 2,3,3-trichloroallyl-N-(alpha-methylbenzyl)dithiocarbamate | 0.5 | 20 | 30 |
| | 0.56 | 2,3,3-trichloroallyl-N-(alpha-methylbenzyl)dithiocarbamate | 0.031 | 5 | 70 |
| | 0.56 | 2,3,3-trichloroallyl-N-(alpha-methylbenzyl)dithiocarbamate | 0.125 | 0 | 75 |
| | 0.56 | 2,3,3-trichloroallyl-N-(alpha-methylbenzyl)dithiocarbamate | 0.5 | 20 | 55 |
| | 1.12 | 2,3,3-trichloroallyl-N-(alpha-methylbenzyl)dithiocarbamate | 0.031 | 35 | 65 |
| | 1.12 | 2,3,3-trichloroallyl-N-(alpha-methylbenzyl)dithiocarbonate | 0.125 | 30 | 70 |
| | 1.12 | 2,3,3-trichloroallyl-N-(alpha-methylbenzyl)dithiocarbamate | 0.5 | 15 | 85 |
| | 2.24 | 2,3,3-trichloroallyl-N-(alpha-methylbenzyl)dithiocarbamate | 0.125 | 60 | 40 |
| | 2.24 | 2,3,3-trichloroallyl-N-(alpha- | 0.5 | 20 | 80 |

TABLE II (A)-continued

| Example No. | Amount of triallate Herbicide (kg./ha.) | Antagonistic Agent | Weight % On Seed Of Antagonistic Agent | Percent Inhibition Of Wheat | Safening Effect (%) |
|---|---|---|---|---|---|
| | | methylbenzyl)dithiocarbamate | | | |
| 180 | 0.14 | Methyl-N-butyldithio-carbanilate | 0.031 | 0 | 35 |
| | 0.14 | Methyl-N-butyldithio-carbanilate | 0.125 | 10 | 25 |
| | 0.14 | Methyl-N-butyldithio-carbanilate | 0.500 | 10 | 25 |
| | 0.28 | Methyl-N-butyldithio-carbanilate | 0.031 | 15 | 60 |
| | 0.28 | Methyl-N-butyldithio-carbanilate | 0.125 | 15 | 60 |
| | 0.28 | Methyl-N-butyldithio-carbanilate | 0.500 | 15 | 60 |
| | 0.56 | Methyl-N-butyldithio-carbanilate | 0.031 | 55 | 43 |
| | 0.56 | Methyl-N-butyldithio-carbanilate | 0.125 | 50 | 48 |
| | 0.56 | Methyl-N-butyldithio-carbanilate | 0.500 | 35 | 63 |

EXAMPLES 181 to 185

These examples illustrate the application of the antagonistic agents of this invention as seed treatments to protect desired crops from herbicidal injury by thiolcarbamate herbicides other than triallate. In these examples the herbicide is applied to the soil as in Examples 1 to 169. However, the antagonistic agent is applied to crop seed as in Examples 170 to 180. The results are tabulated in Table II (B) which show the safening effect of the antagonistic agents of this invention.

In order to counteract injury by the thiolcarbamate herbicide, the crop seed need to treated with only a small amount of the antagonistic agent. For example, application rates of about 1100 g. to as low as about 1.5 g. of active agent per bushel of seed may be used. The presently preferred application rate is in the range of about 3 g. to 550 g. of agent per bushel. The seed is treated with an antagonistic agent by use of conventional seed treating apparatus well known to the art. The seed is thoroughly mixed with the antagonistic agent in the seed treating apparatus, thereby giving a seed which is coated with the agent.

Since only a very small amount of active antagonistic agent is required for the seed treatment, the compound preferably is formulated as a wettable powder or an emulsifiable concentrate which can be diluted with water by the seed treater for use in the seed treating apparatus. Of course, under certain conditions, it may be desirable to dissolve the antagonistic agent in an organic solvent for use as a seed treatment or the pure compound alone may be used under properly controlled conditions.

There are thus also provided by this invention novel seed treating compositions containing one or more of the described active antagonistic agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active antagonistic agent in liquids used as a carrier in which the agent is not completely soluble. Emulsifying agents and wetting agents, also known as "surface active agents", are sold under numerous tradenames and may be either pure compounds, mixtures of compounds of the same general groups, or they may be mixtures of compounds of different classes. Typical satisfactory surface active agents which may be used are alkali metal higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8-18 carbon atoms, long chain quaternary ammonium compounds, sodium salts of petroleum-derived alkylsulfonic acids, polyethylene sorbitan monooleate, alkylaryl polyester alcohols, water-soluble lignin sulfonate salts, alkali casein compositions, long chain alcohols usually containing 10 to 18 carbon atoms, and condensation products of ethylene oxide with fatty acids, alkylphenols and mercaptans.

TABLE II (B)

| Example No. | Amount Herbicide (kg./ha.) | Herbicide | Weight % On Seed Of Antagonistic Agent | Safening Agent | Percent Inhibition Of Wheat | Safening Effect(%) |
|---|---|---|---|---|---|---|
| 181 | 0.28 | diallate | 0.031 | tertiary butylthiol-carbanilate | 85 | 15 |
| | 0.28 | diallate | 0.125 | tertiary butylthiol-carbanilate | 80 | 20 |
| | 0.28 | diallate | 0.5 | tertiary butylthiol-carbanilate | 60 | 40 |
| 182 | 0.28 | diallate | 0.031 | 2,3,3-trichloroallyl-N-alpha-methylbenzyl-dithiocarbamate | 80 | 18 |
| | 0.28 | diallate | 0.125 | 2,3,3-trichloroallyl-N-alpha-methylbenzyl- | 50 | 48 |

TABLE II (B)-continued

| Example No. | Amount Herbicide (kg./ha.) | Herbicide | Weight % On Seed Of Antagonistic Agent | Safening Agent | Percent Inhibition Of Wheat | Safening Effect(%) |
|---|---|---|---|---|---|---|
| | 0.28 | diallate | 0.5 | dithiocarbamate 2,3,3-trichloroallyl-N-alpha-methylbenzyl-dithiocarbamate | 20 | 78 |
| 183 | 0.28 | diallate | 0.031 | methyl-N-ethyldithiocarbanilate | 50 | 40 |
| | 0.28 | diallate | 0.125 | methyl-N-ethyldithiocarbanilate | 25 | 65 |
| | 0.28 | diallate | 0.5 | methyl-N-ethyldithiocarbanilate | 20 | 70 |
| 184 | 0.28 | diallate | 0.031 | methyl-N-methyldithiocarbanilate | 70 | 25 |
| | 0.28 | diallate | 0.125 | methyl-N-methyldithiocarbanilate | 40 | 55 |
| | 0.28 | diallate | 0.5 | methyl-N-methyldithiocarbanilate | 75 | 20 |
| 185 | 0.28 | S-propyl-N-butyl-N-ethylthiolcarbamate | 0.031 | methyl-N-methyldithiocarbanilate | 70 | 15 |
| | 0.28 | S-propyl-N-butyl-N-ethylthiolcarbamate | 0.125 | methyl-N-methyldithiocarbanilate | 40 | 45 |
| | 0.28 | S-propyl-N-butyl-N-ethylthiolcarbamate | 0.5 | methyl-N-methyldithiocarbanilate | 40 | 45 |

EXAMPLES 186 to 205

The procedure of Examples 1 to 169 is followed except that, instead of applying the antagonistic agent as a sequential spray before application of the thiolcarbamate herbicide, the antagonistic agent and thiolcarbamate herbicide are applied to the soil together as a mixture to give the amounts for each shown for each example in Table III. Good control of weeds is noted in each example.

TABLE III

| Example No. | Amount Herbicide (kg./ha.) | Herbicide | Amount Antagonistic Agent (kg./ha.) | Antagonistic Agent | Crop | Percent Inhibition | Safening Effect (%) |
|---|---|---|---|---|---|---|---|
| 186 | 0.28 | diallate | 8.96 | allyl-N-methyldithiocarbanilate | Wheat | 70 | 20 |
| | 0.28 | diallate | 8.96 | allyl-N-methyldithiocarbanilate | Sorghum | 50 | 47 |
| | 0.28 | diallate | 8.96 | methyl-N-ethyldithiocarbanilate | Wheat | 20 | 70 |
| | 0.28 | diallate | 8.96 | methyl-N-ethyldithiocarbanilate | Sorghum | 65 | 32 |
| 187 | 0.28 | S-ethyl-N,N-dipropylthiolcarbamate | 8.96 | allyl-N-methyldithiocarbanilate | Wheat | 60 | 13 |
| | 0.28 | S-ethyl-N,N-dipropylthiolcarbamate | 8.96 | allyl-N-methyldithiocarbanilate | Sorghum | 70 | 22 |
| 188 | 0.28 | S-ethyl-N-ethyl-N-cyclohexane-thiolcarbamate | 8.96 | allyl-N-methyldithiocarbanilate | Sorghum | 60 | 15 |
| 189 | 0.28 | triallate | 8.96 | allyl-N-methyldithiocarbanilate | Wheat | 55 | 42 |
| | 0.28 | triallate | 8.96 | alyl-N-methyldithiocarbanilate | Sorghum | 15 | 84 |
| 190 | 0.28 | triallate | 8.96 | methyl-N-ethyldithiocarbanilate | Wheat | 25 | 72 |
| | 0.28 | triallate | 8.96 | methyl-N-ethyldithiocarbanilate | Sorghum | 55 | 44 |
| | 8.96 | triallate | 8.96 | methyl-N-ethyldithiocarbanilate | Sorghum | 75 | 24 |
| 191 | 0.28 | S-propyl-N-butyl-N-ethylthiocarbamate | 8.96 | allyl-N-methyldithiocarbanilate | Sorghum | 60 | 38 |
| 192 | 0.28 | S-propyl-N-butyl-N-ethylthiolcarbamate | 8.96 | methyl-N-ethyldithiocarbanilate | Sorghum | 70 | 28 |
| 193 | 0.28 | S-ethyl-N,N-diisobutylthiolcarbamate | 8.96 | allyl-N-methyldithiocarbanilate | Sorghum | 65 | 23 |
| 194 | 0.28 | S-ethyl-N,N-diisobutylthiolcarbamate | 8.96 | methyl-N-ethyldithiocarbanilate | Sorghum | 75 | 13 |
| 195 | 0.28 | S-propyl-N,N- | 8.96 | allyl-N-methyldithiocarbanilate | Sorghum | 75 | 15 |

TABLE III-continued

| Example No. | Amount Herbicide (kg./ha.) | Herbicide | Amount Antagonistic Agent (kg./ha.) | Antagonistic Agent | Crop | Percent Inhibition | Safening Effect (%) |
|---|---|---|---|---|---|---|---|
|  |  | dipropylthiolcarbamate |  | carbanilate |  |  |  |
| 196 | 8.96 | diallate | 8.96 | allyl-N-methyldithiocarbanilate | Corn | 5 | 30 |
| 197 | 8.96 | S-ethyl-N,N-dipropylthiolcarbamate | 8.96 | allyl-N-methyldithiocarbanilate | Corn | 30 | 45 |
| 198 | 8.96 | S-ethyl-N,N-dipropylthiolcarbamate | 8.96 | methyl-N-ethyldithiocarbanilate | Corn | 40 | 35 |
| 199 | 8.96 | S-ethyl-N-ethyl-thiolcyclohexane-carbamate | 8.96 | methyl-N-ethyldithiocarbanilate | Corn | 65 | 23 |
| 200 | 8.96 | triallate | 8.96 | allyl-N-methyldithiocarbanilate | Corn | 10 | 25 |
| 201 | 8.96 | triallate | 8.96 | methyl-N-ethyldithiocarbanilate | Corn | 10 | 25 |
| 202 | 8.96 | S-propyl-N-butyl-N-ethylthiolcarbamate | 8.96 | allyl-N-methyldithiocarbanilate | Corn | 70 | 10 |
| 203 | 8.96 | S-propyl-N-butyl-N-ethylthiolcarbamate | 8.96 | methyl-N-ethyldithiocarbanilate | Corn | 60 | 20 |
| 204 | 8.96 | S-propyl-N,N-dipropylthiolcarbamate | 8.96 | allyl-N-methyldithiocarbanilate | Corn | 55 | 28 |
| 205 | 8.96 | S-propyl-N,N-dipropylthiolcarbamate | 8.96 | methyl-N-ethyldithiocarbanilate | Corn | 70 | 13 |

EXAMPLE 206

This example illustrates the safening effect of a representative antagonistic agent of this invention, methyl-N-ethyldithiocarbanilate, as a wheat seed treatment with a representative thiolcarbamate herbicide, triallate, applied as a pre-emergent herbicide after the treated wheat seed is planted in a number of different soil types. The procedure of Examples 170 to 185 is employed and the soil in which the treated wheat seed is planted is as designated in Table IV. Good weed control and safening of the herbicide is noted for each soil type.

TABLE IV

| Amount of triallate herbicide (kg/ha) | Soil Type | Amount of methyl-N-ethyl-dithiocarbanilate antagonistic agent applied as a seed treatment (weight %) | Inhibition of Wheat (percent) | Safening Effect (percent) |
|---|---|---|---|---|
| 2.24 | Ray silt loam | 0.25 | 75 | 18 |
| 2.24 | Florida sand | 0.25 | 28 | 45 |
| 2.24 | Norfolk sandy loam | 0.25 | 25 | 40 |
| 2.24 | Drummer silty clay loam | 0.25 | 55 | 38 |
| 2.24 | Sarpy silty clay loam | 0.25 | 65 | 23 |
| 2.24 | Wabash silty clay loam | 0.25 | 60 | 30 |

EXAMPLE 207

This example illustrates the use of a representative antagonistic agent, methyl-N-ethyldithiocarbanilate, as a wheat seed treatment formulated with a variety of carriers to safen the plant inhibition effect on wheat of a representative thiolcarbamate herbicide. The procedure of Examples 170 to 185 is followed except that the carriers designated in Table V are employed with the results shown. In each instance good control of weeds is observed.

TABLE V

| Amount of triallate herbicide (kg/ha) | Carrier | Amount of methyl-N-ethyl-dithiocarbanilate antagonistic agent applied as a seed treatment (weight %) | Inhibition of Wheat (percent) | Safening Effect (percent) |
|---|---|---|---|---|
| 0.56 | acetone | 0.25 | 15 | 55 |
| 0.56 | methanol | 0.25 | 15 | 55 |
| 0.56 | ethanol | 0.25 | 20 | 50 |
| 0.56 | isopropanol | 0.25 | 20 | 50 |
| 0.56 | 20 percent by weight of dimethylsulfoxide in acetone | 0.25 | 30 | 40 |
| 0.56 | dichloromethane | 0.25 | 13 | 57 |
| 0.56 | ethyl acetate | 0.25 | 23 | 47 |
| 0.56 | toluene | 0.25 | 15 | 55 |
| 0.56 | powder formulation 30 percent by weight | 0.25 | 18 | 52 |

TABLE V-continued

| Amount of triallate herbicide (kg/ha) | Carrier | Amount of methyl-N-ethyl-dithiocarbanilate antagonistic agent applied as a seed treatment (weight %) | Inhibition of Wheat (percent) | Safening Effect (percent) |
|---|---|---|---|---|
| 0.56 | dipropylene glycol 20 percent by weight calcium silicate 95 percent by weight kaolinite 1.5 percent by weight dipropylene glycol 1 percent by weight calcium silicate | 0.25 | 13 | 57 |

EXAMPLES 208 TO 213

These examples illustrate the application of representative antagonistic agents of this invention as seed treatments to protect corn (maize) from herbicidal injury by thiolcarbamate herbicides. In these examples the herbicide is applied to the soil as in Examples 1 to 169. However, the antagonistic agent is applied to corn seed as in Examples 170 to 186. The results are tabulated in Table VI which show the safening effect of the antagonistic agents of this invention as seed treatment on corn. Good control of weeds is noted for each example.

TABLE VI

| Example No. | Amount Herbicide (kg./ha.) | Herbicide | Weight % On Corn Seed Of Antagonistic Agent | Antagonistic Agent | Percent Inhibition Of Corn | Safening Effect (%) |
|---|---|---|---|---|---|---|
| 208 | 8.96 | diallate | 0.031 | Methyl-N-methyl-dithiocarbanilate | 60 | 5 |
|  | 8.96 | diallate | 0.125 | Methyl-N-methyl-dithiocarbanilate | 25 | 35 |
|  | 8.96 | diallate | 0.5 | Methyl-N-methyl-dithiocarbanilate | 10 | 50 |
| 209 | 8.96 | EPTC | 0.5 | Methyl-N-methyl-dithiocarbanilate | 40 | 25 |
| 210 | 8.96 | vernolate | 0.031 | Methyl-N-methyl-dithiocarbanilate | 85 | 5 |
|  | 8.96 | vernolate | 0.125 | Methyl-N-methyl-dithiocarbanilate | 40 | 50 |
|  | 8.96 | vernolate | 0.5 | Methyl-N-methyl-dithiocarbanilate | 40 | 50 |
| 211 | 8.96 | pebulate | 0.5 | Methyl-N-methyl-dithiocarbanilate | 45 | 35 |
| 212 | 8.96 | diallate | 0.125 | Methyl-N-ethyl-dithiocarbanilate | 30 | 10 |
|  | 8.96 | diallate | 0.5 | Methyl-N-ethyl-dithiocarbanilate | 10 | 30 |
| 213 | 8.96 | butylate | 0.031 | Methyl-N-ethyl-dithiocarbanilate | 0 | 25 |
|  | 8.96 | butylate | 0.125 | Methyl-N-ethyl-dithiocarbanilate | 0 | 25 |
|  | 8.96 | butylate | 0.5 | Methyl-N-ethyl-dithiocarbanilate | 0 | 25 |

While this invention has been described with respect to certain embodiments, it is to be understood that it is not so limited and that variations and modifications thereof obvious to those skilled in the art to which this invention appertains can be made without departing from the spirit or scope thereof.

What is claimed is:

1. A method for reducing injury to wheat, sorghum and corn by thiolcarbamate herbicides selected from the group consisting of S-2-dichloroallyl N,N-diisopropylthiocarbamate and S-2,3,3-trichloroallyl N,N-diisopropylthiocarbamate which comprises applying to the soil, crop or crop seed an effective safening amount of a compound of the formula

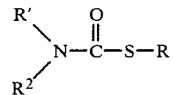

wherein R is lower alkyl, R' is hydrogen and $R^2$ is phenyl.

2. A method of claim 1 wherein the compound is incorporated into the soil.
3. Method of claim 1 wherein R is tert-butyl.
4. A safened herbicide composition comprising a thiolcarbamate herbicide selected from the group consisting of S-2,3-dichloroallyl N,N-diisopropylthiolcarbamate and S-2,3,3-trichloroallyl N,N-diisopropylthiolcarbamate and an effective safening amount of a compound of the formula

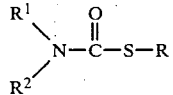

wherein R is lower alkyl, $R^1$ is hydrogen and $R^2$ is phenyl.

5. Composition of claim 4 wherein R is tert-butyl.

* * * * *

UNITED STATES PATENT AND TRADEMARK OFFICE
CERTIFICATE OF CORRECTION

PATENT NO. : 4,231,786
DATED : Nov. 4, 1980
INVENTOR(S) : Albert J. Czajkowski, Maryland Heights, Mo.
David E. Schafer, St. Louis, Mo.

It is certified that error appears in the above-identified patent and that said Letters Patent is hereby corrected as shown below:

Column 2, line 53, delete "very" and insert -- vary --.

Column 2, line 68, delete "if" and insert -- of --.

Column 26, line 49, delete "polyester" and insert -- polyether --.

Column 31, line 63, delete, "S-2-dichloroally" and insert -- S-2,3-dichloroallyl --.

Signed and Sealed this

First Day of November 1983

[SEAL]

Attest:

Attesting Officer

GERALD J. MOSSINGHOFF

Commissioner of Patents and Trademarks